US012447036B2

(12) United States Patent
Tao

(10) Patent No.: US 12,447,036 B2
(45) Date of Patent: Oct. 21, 2025

(54) TOE CORRECTOR

(71) Applicant: Ping Tao, Guangdong (CN)

(72) Inventor: Ping Tao, Guangdong (CN)

( * ) Notice: Subject to any disclaimer, the term of this patent is extended or adjusted under 35 U.S.C. 154(b) by 285 days.

(21) Appl. No.: 18/300,130

(22) Filed: Apr. 13, 2023

(65) Prior Publication Data

US 2024/0315863 A1 Sep. 26, 2024

(30) Foreign Application Priority Data

Mar. 22, 2023 (CN) ......................... 202320569338.3

(51) Int. Cl.
*A61F 5/00* (2006.01)
*A61F 5/01* (2006.01)

(52) U.S. Cl.
CPC .................................... *A61F 5/019* (2013.01)

(58) Field of Classification Search
CPC .... A61F 5/019; A61F 5/0127; A61F 5/05875; A61F 5/058; A61F 5/10; A61F 5/11; A61F 2005/0137; A61B 17/54; A43B 7/26
USPC ...................................................... 602/30, 22
See application file for complete search history.

(56) References Cited

U.S. PATENT DOCUMENTS 3,662,435 A * 5/1972 Allsop ............... A43C 11/1413 24/70 SK
6,149,616 A * 11/2000 Szlema .................... D04B 1/18 602/26

OTHER PUBLICATIONS

CN 211962310 U (Year: 2020).*
KR 20220000406 U (Year: 2022).*

* cited by examiner

*Primary Examiner* — Kim M Lewis

(57) ABSTRACT

A toe corrector comprising a corrector base with a toe bandage and a sole bandage provided thereon to cooperate with said corrector base; the toe corrector also includes an adjusting rope on the corrector base and an angle adjusting mechanism is provided to connect with the adjusting rope; said angle adjusting mechanism includes a rack belt and a latch adjusting component; one end of the rack belt is connected with the adjusting rope while the other end thereof passes the latch adjusting component; the position of the rack belt is adjusted through latch adjusting component. The invention adopts latch mechanism component to realize adjustment of the position of the rack belt, which can save more labor and avoid short rack broken or rack skipping effectively.

6 Claims, 6 Drawing Sheets

TOE CORRECTOR

BACKGROUND OF THE INVENTION

1. Field of the Invention

The invention relates to the technical field of a toe corrector, specifically relating to a type of toe corrector.

2. Description of the Related Art

Toe valgus is divided into congenital toe valgus and acquired toe valgus. The acquired toe valgus is dominated by hallux valgus. Congenital toe valgus mainly refers to congenital equinovarus or toe valgus caused by sequela of poliomyelitis. Toe valgus caused by poliomyelitis sequela, encephalitis or congenital equinovarus is mainly manifested by uprising toes and skeletal imbalance of muscles and tendons. A toe corrector is used during the treatment of toe valgus.

The knob adjustment on the existing market can not save labor, and due to the limitation of the volume, the internal rack is very small and the borne force thereof is also small, short rack broken or rack skipping can happen in the using process.

Therefore, a toe corrector becomes a problem that needs solving throughout society.

SUMMARY OF THE INVENTION

In order to solve above technical problem, the invention provides a technical scheme as follows: a toe corrector comprises a corrector base with a toe bandage and a sole bandage provided thereon to cooperate with said corrector base; the toe corrector also includes an adjusting rope on the corrector base and an angle adjusting mechanism is provided to connect with the adjusting rope; said angle adjusting mechanism includes a rack belt and a latch adjusting component; one end of the rack belt is connected with the adjusting rope while the other end thereof passes the latch adjusting component; the position of the rack belt is adjusted through latch adjusting component.

Furthermore, the latch adjusting component comprises a latch mechanism component, a supporting base and a limiting latch; said supporting base is arranged on the corrector base, said latch mechanism component is connected with the supporting base in a rotating manner via rivets, the bottom end of said latch mechanism component is provided with latches corresponding to racks on the rack belt, and the bottom of said limiting latch is matched with racks on the rack belt.

Furthermore, the mating holes are provided on the latch mechanism component to cooperate with the top end of the limiting latch, and said limiting latch is fixed on the supporting base via rivets.

Compared with the prior art, the invention has following advantages:

The invention adopts latch mechanism component to realize adjustment of the position of the rack belt, which can save more labor and avoid short rack broken or rack skipping effectively.

Figure 1:
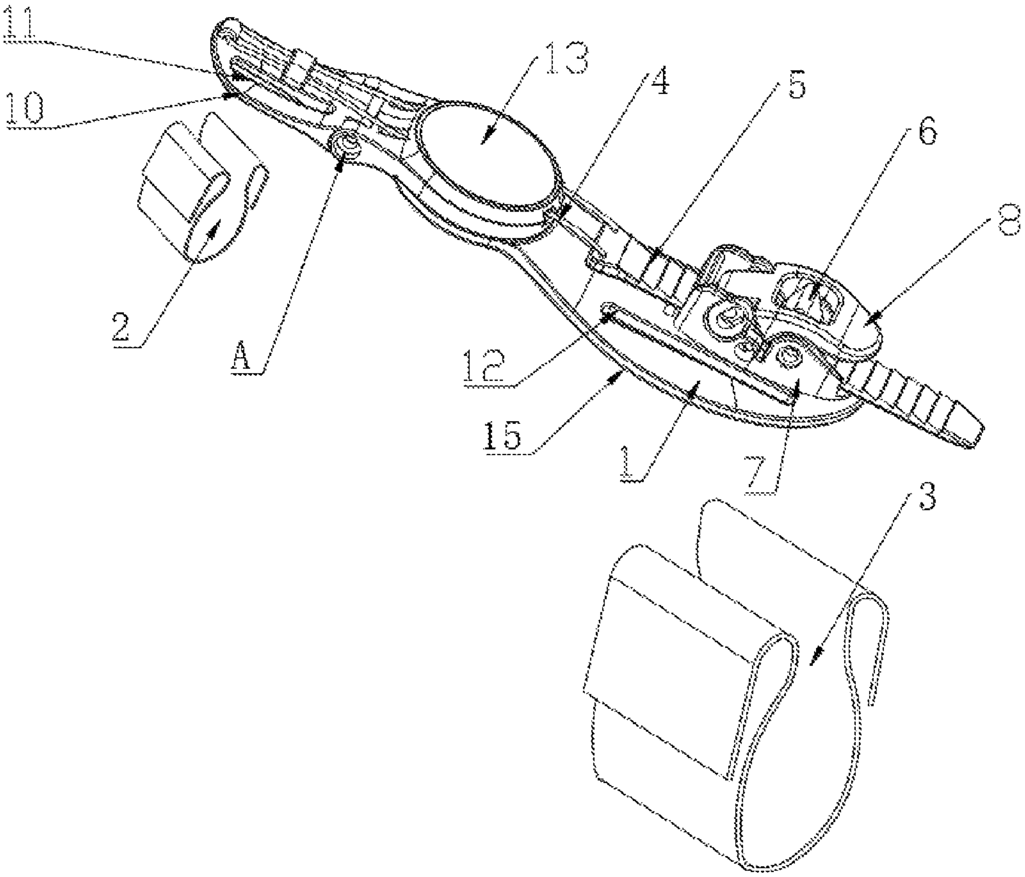
FIG. 1 is the structural diagram of the toe corrector of the invention.
Figure 2:
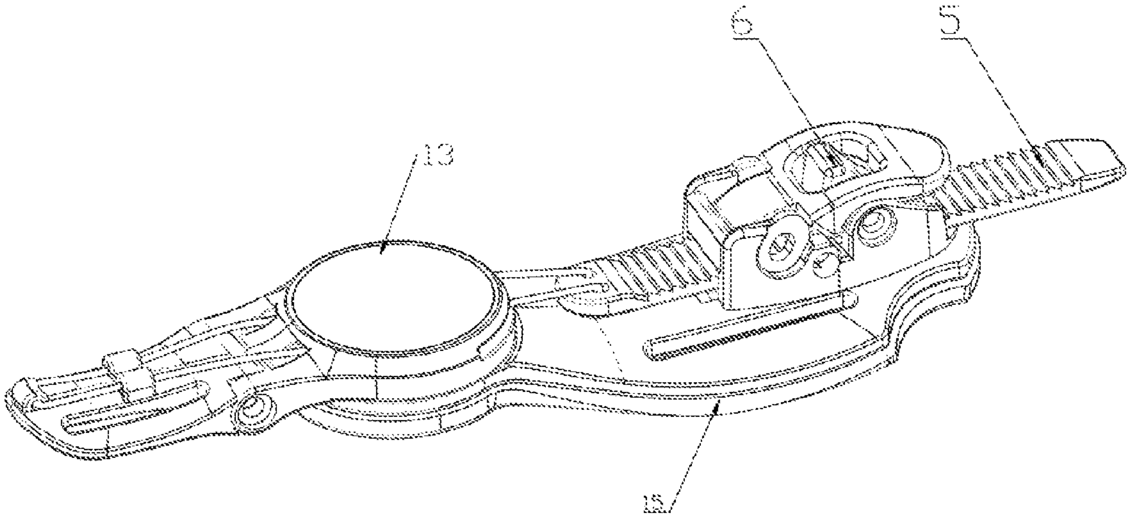
FIG. 2 is the structural diagram of taking off the toe bandage and the sole bandage.
Figure 3:
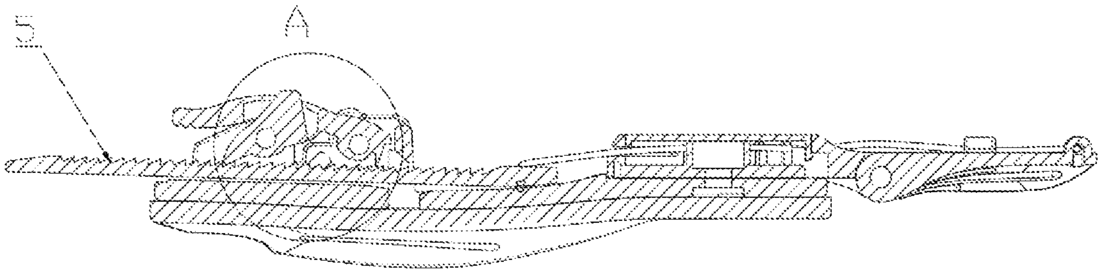
FIG. 3 illustrates the sectional view of the toe corrector of the invention.
Figure 4:
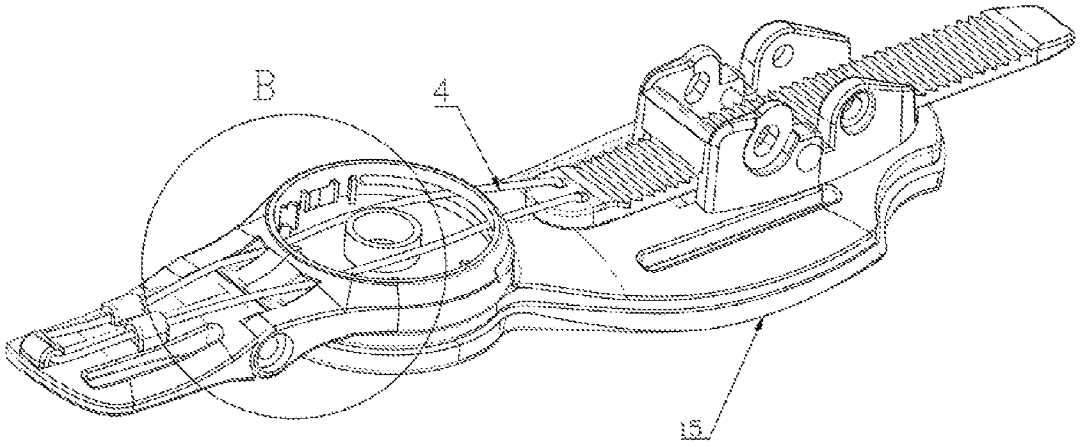
FIG. 4 is illustrates the interior view of the toe corrector of the invention.
Figure 5:
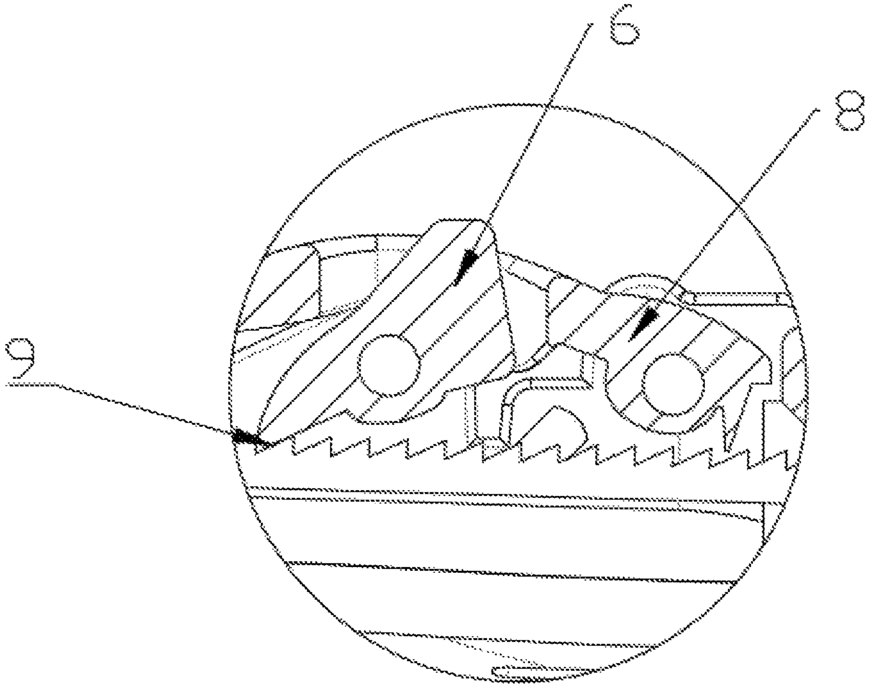
FIG. 5 is the partial enlarged view of area A in FIG. 2.
Figure 6:
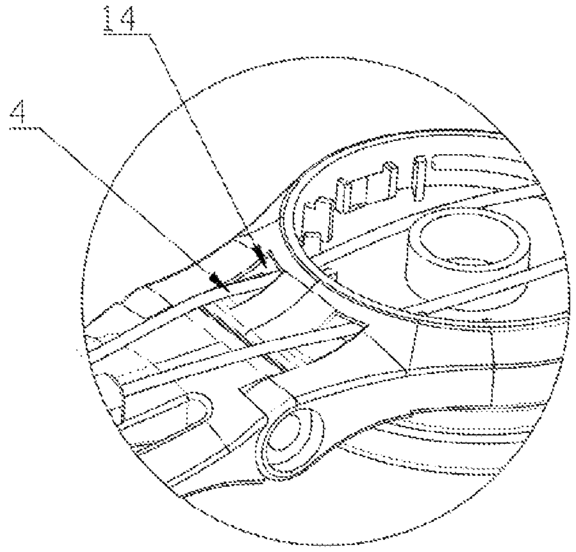
FIG. 6 is the partial enlarged view of area B in FIG. 3.

As shown: 1. corrector base, 2. toe bandage, 3. sole bandage, 4. adjusting rope, 5. rack belt, 6. latch mechanism component, 7. supporting base, 8. limiting latch, 9. latch, 10. toe pad, 11. the first fixing hole, 12. the second fixing hole, 13. annular housing, 14. hole, 15. liquid silicone pad Area A in FIG. 1 is where the rivet locates.

DETAILED DESCRIPTION OF THE PREFERRED EMBODIMENTS

The invention is further described in detail hereinafter with reference to the drawings. The invention is described in detail with reference to the drawings.

The invention provides a toe corrector in the preferred embodiment comprising a corrector base 1 with a toe bandage 2 and a sole bandage 3 provided thereon to cooperate with said corrector base 1; the toe corrector also includes an adjusting rope 4 on the corrector base 1 and an angle adjusting mechanism is provided to connect with the adjusting rope 4; said angle adjusting mechanism includes a rack belt 5 and a latch adjusting component; one end of said rack belt 5 is connected with the adjusting rope 4 while the other end thereof passes the latch adjusting component; the position of the rack belt 5 is adjusted through latch adjusting component, which can save labor and time remarkably.

As a further illustration of the invention, said latch adjusting component comprises a latch mechanism component 6, a supporting base 7 and a limiting latch 8; said supporting base 7 is arranged on the corrector base 1, said latch mechanism component 6 is connected with the supporting base 7 in a rotating manner via rivets, the bottom end of said latch 6 mechanism component is provided with latches 9 corresponding to racks on the rack belt 5, and the bottom of said limiting latch 8 is matched with racks on the rack belt 5. The cooperation among the latch mechanism component 6, the limiting latch 8 and the rack belt 5 can effectively avoid short rack breaking or rack skipping during using.

As a further illustration of the invention, mating holes are provided on said latch mechanism component 6 to cooperate with the top end of the limiting latch 8, and said limiting latch 8 is fixed on the supporting base 7 via rivets.

As a further illustration of the invention, a front end of said corrector base 1 is provided with a toe pad 10 connected in a rotating manner and one end of the adjusting rope 4 that is far from the rack belt 5 is fixed on the toe pad 10.

As a further illustration of the invention, two groups of the first fixing holes 11 are provided on said toe pad 10; one end of said toe bandage 2 is fixed on a first fixing hole 11 while the other end thereof passes another first fixing hole 11 and is fixed via hook and loop. The tightness of the toe position can be adjusted via the tightness of the hook and loop.

As a further illustration of the invention, two groups of the second fixing holes 12 are provided on said corrector base 1; one end of said sole bandage 3 is fixed on a second fixing hole 12 while the other end thereof passes another second fixing hole 12 and is fixed via hook and loop. The tightness of the sole position can be adjusted via the tightness of the hook and loop.

As a further illustration of the invention, said corrector base 1 is provided with an annular housing 13 at one end close to the toe pad 10, and the annular housing 13 is provided with a hole 14 for the adjusting rope 4 to pass through. The annular housing 13 adds to the aesthetic appearance of the overall toe corrector.

As a further illustration of the invention, a liquid silicone pad 15 is attached to the bottom of said corrector base 1, which has the characteristics of softness like human skin, no odor and no toxicity, it can effectively protect soles and prevent soles from directly contacting and rubbing with the bracket for a long time to abrade the skin.

The specific working process of the invention is as follows:

The invention discloses when using, place the corrector base 1 on the sole side that is close to the big toe, utilize toe bandage 2 and sole bandage 3 to fix toe and sole respectively, and adjust the tightness of the toe bandage 2 tying up the toe and sole bandage 3 tying up the sole by the hook and loop.

After the toe corrector is fixed, shifting the latch mechanism component 6 upwards by hand; as the latch 9 corresponding to the rack on the rack belt 5 is arranged at the bottom of the latch mechanism component 6, the rack belt 5 moves outwards under the action of the latch 9, accordingly the adjusting rope 4 is driven to pull the toe pad 10 backwards and the toe is pulled to turn outwards, achieving effect of adjusting toes.

Because said latch mechanism component 6 is rotatably connected with the supporting base 7 via rivets and lever principle is adopted, just stirring latch mechanism component 6 gently can adjust. It has strong practicality as very little strength applied can realize adjustment.

The liquid silicone pad 15 is attached to the bottom of said corrector base 1, which has the characteristics of softness like human skin, no odor and no toxicity, it can effectively protect soles and prevent soles from directly contacting and rubbing with the bracket for a long time to abrade the skin.

The invention and its embodiments have been described above, but the description is not limited thereto; only one embodiment of the invention is shown in the drawings, and the actual structure is not limited thereto. In general, it is to be understood by those skilled in the art that non-creative design of structural forms and embodiments that are similar to the technical solutions without departing from the spirit of the invention shall all fall within the protective scope of the invention.

What is claimed is:

1. A toe corrector comprising a corrector base (1) with a toe bandage (2) and a sole bandage (3) provided thereon to cooperate with said corrector base (1); the toe corrector also includes an adjusting rope (4) on the corrector base (1) and an angle adjusting mechanism is provided to connect with said adjusting rope (4); said angle adjusting mechanism includes a rack belt (5) and a latch adjusting component; one end of said rack belt (5) is connected with the adjusting rope (4) while the other end thereof passes the latch adjusting component; the position of the rack belt (5) is adjusted through latch adjusting component;

wherein said latch adjusting component comprises a latch mechanism component (6), a supporting base (7) and a limiting latch (8); said supporting base (7) is arranged on the corrector base (1), said latch mechanism component (6) is connected with the supporting base (7) in a rotating manner via rivets, a bottom end of said latch mechanism component (6) is provided with latches (9) corresponding to racks on the rack belt (5), and a bottom of said limiting latch (8) is matched with racks on the rack belt (5);

wherein mating holes are provided on said latch mechanism component (6) to cooperate with a top end of the limiting latch (8), and said limiting latch (8) is fixed on the supporting base (7) via rivets.

2. The toe corrector of claim 1 wherein a front end of said corrector base (1) is provided with a toe pad (10) connected in a rotating manner and one end of the adjusting rope (4) that is far from the rack belt (5) is fixed on the toe pad (10).

3. The toe corrector of claim 2 wherein two groups of first fixing holes (11) are provided on said toe pad (10); one end of said toe bandage (2) is fixed on a first fixing hole (11) while the other end thereof passes another first fixing hole (11) and is fixed via hook and loop.

4. The toe corrector of claim 1 wherein two groups of second fixing holes (12) are provided on said corrector base (1); one end of said sole bandage (3) is fixed on a second fixing hole (12) while the other end thereof passes another second fixing hole (12) and is fixed via hook and loop.

5. The toe corrector of claim 1 wherein said corrector base (1) is provided with an annular housing (13) at one end close to the toe pad (10), and the annular housing (13) is provided with a hole (14) for the adjusting rope (4) to pass through.

6. The toe corrector of claim 1 wherein a liquid silicone pad (15) is attached to a bottom of said corrector base (1).

* * * * *